United States Patent
Hulls

(10) Patent No.: US 10,023,504 B2
(45) Date of Patent: Jul. 17, 2018

(54) COMPOSTING SYSTEM AND METHOD

(71) Applicant: John Hulls, Point Reyes, CA (US)

(72) Inventor: John Hulls, Point Reyes, CA (US)

( * ) Notice: Subject to any disclaimer, the term of this patent is extended or adjusted under 35 U.S.C. 154(b) by 193 days.

(21) Appl. No.: 14/889,817

(22) PCT Filed: May 14, 2014

(86) PCT No.: PCT/US2014/038007
§ 371 (c)(1),
(2) Date: Nov. 6, 2015

(87) PCT Pub. No.: WO2014/186471
PCT Pub. Date: Nov. 20, 2014

(65) Prior Publication Data
US 2016/0102026 A1    Apr. 14, 2016

Related U.S. Application Data

(60) Provisional application No. 61/823,857, filed on May 15, 2013.

(51) Int. Cl.
*C05F 17/02*  (2006.01)
*C05F 17/00*  (2006.01)
(Continued)

(52) U.S. Cl.
CPC ............ *C05F 17/0258* (2013.01); *C05F 3/00* (2013.01); *C05F 3/04* (2013.01); *C05F 3/06* (2013.01);
(Continued)

(58) Field of Classification Search
CPC .......... C05F 3/00; C05F 3/04; C05F 17/0036; C05F 17/02; C05F 3/06; C05F 17/00;
(Continued)

(56) References Cited

U.S. PATENT DOCUMENTS 3,916,456 A * 11/1975 Persson .................. A47K 11/02
4/111.5
3,936,975 A * 2/1976 de Winter .............. A01G 18/60
47/1.1
(Continued)

OTHER PUBLICATIONS

PCT/US2014/038007—International Search Report and Written Opinion.
(Continued)

*Primary Examiner* — Gautam Prakash
(74) *Attorney, Agent, or Firm* — John Storella, P.C.

(57) ABSTRACT

This disclosure provides a composting system and method. The system comprises: (a) a container configured to contain a composition and comprising (i) insulated walls, (ii) an air intake and (iii) a vent; and (b) a composition contained in the container. The composition comprises aerobic microorganisms, a carbon source and a nutrient source sufficient to support growth of the aerobic microorganisms. The container is sufficiently insulated so that heat generated by aerobic respiration is sufficiently retained in the container to maintain a heat gradient in the container. The container is dimensioned to generate a stack effect that moves air into the air intake, through the composition and out the vent. The moving air provides oxygen to support growth of aerobic microorganisms, making the stack effect self-sustaining as long as a carbon source and nutrients last. The insulation can maintain temperatures in the composting cell sufficient to kill pathogenic microorganisms.

11 Claims, 4 Drawing Sheets

(51) Int. Cl.
*C05F 3/06* (2006.01)
*C05F 3/04* (2006.01)
*C05F 3/00* (2006.01)

(52) U.S. Cl.
CPC .......... *C05F 17/00* (2013.01); *C05F 17/0036* (2013.01); *C05F 17/02* (2013.01); *Y02E 50/343* (2013.01); *Y02P 20/145* (2015.11); *Y02W 30/43* (2015.05); *Y02W 30/47* (2015.05)

(58) Field of Classification Search
CPC ... C05F 17/0258; Y02W 30/47; Y02W 30/43; Y02E 50/343; Y02P 20/145
See application file for complete search history.

(56) References Cited

U.S. PATENT DOCUMENTS

| | | |
|---|---|---|
| 4,302,236 A | 11/1981 | Roman |
| 4,552,484 A | 11/1985 | Nuttle |
| 5,228,984 A | 7/1993 | Lindstrom |
| 5,633,163 A | 5/1997 | Cameron |
| 5,879,931 A | 3/1999 | Kim |
| 7,824,903 B2 | 11/2010 | O'Neill |
| 2007/0111305 A1 | 5/2007 | O'Neill |
| 2011/0311406 A1 | 12/2011 | Wilson |
| 2012/0021504 A1 | 1/2012 | Bradlee |
| 2012/0165215 A1 | 6/2012 | Andersen |

OTHER PUBLICATIONS

San Joaquin Valley Techology Advancement Program, "Greewaste Compose Site Emissions Reductions from Solar-powered Aeration and Biofilter Layer" May 14, 2013.

Composting Council of Canada, "Composting Processing Technologies".

Bryan-Brown, "Lessons Learned in Aerated Static Pile (ASP) Composting".

* cited by examiner

COMPOSTING SYSTEM AND METHOD

CROSS-REFERENCE TO RELATED APPLICATIONS

This application is a National Stage entry of PCT/US2014/038007, filed May 14, 2014, which claims the benefit of the filing date of United States provisional patent application 61/823,857, filed May 15, 2013.

STATEMENT AS TO FEDERALLY SPONSORED RESEARCH

None.

BACKGROUND OF THE INVENTION

In composting, microorganisms decompose organic matter into compost. This compost can be useful as fertilizer. Materials necessary for composting include a carbon source, a nutrient source (in particular a nitrogen source), water and oxygen. When materials are combined, aerobic microorganisms metabolize the organic material to produce compost. This metabolism also generates heat. Sometimes this can be seen as steam rising from a compost pile.

Oxygen must be available to an aerobic composting system for use by aerobic microorganisms. In dynamic composting systems, the compostable materials are periodically turned to expose them to fresh air. In static composting systems, the compostable materials are not turned and must be aerated by various means.

Static composting methods include in-vessel composting and open-pile composting. In open-pile composting, the compostable material is piled on the ground or on a platform, and possibly covered with coversheet. In in-vessel composting, organic material is contained within a walled container. In both cases, oxygen must be provided to the compost pile. For air to move through the pile, the pile cannot exceed a certain density, e.g., no more than about 800 pounds per cubic yard, and must contain sufficient air passages to permit flow to bring air in contact with the aerobic bacteria. A solid homogeneous material is disadvantageous for aerobic composting.

In forced aeration systems, air is forced into the compost pile. Forced aeration systems include positive aeration and negative aeration. In positive aeration systems, air is pumped into the compost pile. This can be done, for example, by providing perforated pipes through the base of the pile. Air is pumped into the pipes. In negative aeration systems, air is suctioned into the pile. Both systems require energy to force the air through the pile.

Vegetable material (e.g., greenwaste) is a common carbon source used in composting. Certain animal-based materials also provide nutrients, such as nitrogen. Animal products can be rich in nitrogen and also have been used as a source of nitrogen. This includes, for example, animal excrement (manure). Human excrement (urine and/or feces) (also called "night soil" or "humanure") also has been used in composting. However, animal excrement, including human excrement, can include microorganisms pathogenic to humans. To use compost made from such materials as fertilizer, such pathogens must be reduced or eliminated.

U.S. Pat. No. 4,552,484 refers to a system for field disposal of human feces through the use of composting containers that prevent the spread of intestinal bacteria, including virulent pathogens, which otherwise would occur when wilderness visitors practice shallow burial of feces. This is said to be accomplished by providing biodegradable containers and following a pre-set method of disposal.

U.S. Pat. No. 5,228,984 refers to a system and method for composting feces and treating. Human feces is said to be collected within a composting retainer and exposed to sufficient air and water to allow the feces to compost, thereby forming compost product. Urine is said to be collected within an urine treatment retainer which is at least partially partitioned from the composting retainer and wherein the urine is passed through a substrate supporting aerobic nitrifying bacteria, thereby nitrifying a significant portion of the ammonium ions in the urine to form liquid product. The compost product is said to be suitable for subsequent use, such as fertilizer or for use in forming a mixture with soil to form topsoil.

U.S. Pat. No. 5,879,931 refers to an aerobic fermentation promoting device, a fermentation system and organic compost prepared by the system. The device is said to promote aerobic fermentation of compost materials by periodically mixing the compost materials together and by letting the compost materials come into contact with the outside air. The device is said to be installed in a fermentation tank and has a rotatable screw conveyor unit, at least one bucket elevator, a drive unit and a steering unit. The compost is said to be produced by charging moisture control materials in the tank, uniformly spraying excrement on the surface of the moisture control materials, mixing the compost materials together using the fermentation promoting device after lapse of four to seven days since spraying of the excrement, and adding new moisture control materials and new excrement to existing compost materials.

U.S. Patent Application 2007-0111305 refers to systems and methods for the generation of compost. In one embodiment, the system for generating compost is said to comprise an aeration floor having a plurality of gas flow apertures that connect to a network of gas flow channels, and a compost cover constructed of a gas and liquid impermeable fabric that is provided with a plurality of ports that permit the passage of gas and liquid through the compost cover. A compost biomass is said to be placed on the aeration floor and the compost cover is placed over the compost biomass. An air suction manifold, connected to an outlet of the gas flow channels, is said to draw exhaust gases from the compost biomass, through the plurality of gas flow apertures and through the gas flow channels. The exhaust gases are then said to be conveyed to an air distributor and directed to an odor control device for substantially eliminating odors.

U.S. Patent Application 2012-0165215 refers to methods and systems for designing and using organism-specific and/or operational taxon unit (OTU)-specific probes.

U.S. Pat. No. 782,493 refers to systems and methods for generating compost.

The statements in the Background are not necessarily meant to endorse the characterization in the cited references nor are the cited references admitted prior art.

SUMMARY OF THE INVENTION

This disclosure provides, among other things, a system useful for composting, in particular, for composting material such as feces that may comprise pathogenic material. In one embodiment, the system includes a container configured to contain a composition and comprising (i) insulation, (ii) an air intake and (iii) a vent. A composition is provided to the container, which composition comprises (i) aerobic microorganisms, (ii) a carbon source and (iii) a nutrient source (such as feces) sufficient to support growth of the aerobic microorganisms in an aerobic environment. Prior to mixing, the waterborne waste/feces mixture may be in an anaerobic state. Mixing the composition prior to adding the mixture to the container adds oxygen, and creates passages for air flow, thus promoting the growth of aerobic bacteria which are present, and rapidly eliminates the odors from the anaerobic bacteria. An aerobic environment is maintained in the composition by providing air through a convection current referred to as a "stack effect" that moves air into the air intake, and out the vent in such a way to distribute air to the base of the composition and thus to the aerobic microorganisms. The configuration of the container is such that the flow path of the heated air is generally vertical. The vertical flow of the air current is maintained by heating the air in the composition with heat generated by aerobic microorganisms through aerobic respiration, and contained in the container through insulation provided, for example, by walls of the container. This lowers the density of the air in the composting material above the air intake and causing flow from the increased pressure of the more dense air beneath the material, thus creating what is called a "stack effect". The stack effect uses the heat convection from the composting material to create a draft akin to that of a fireplace drawing air up a chimney, with the heat of the respiring microbial mass representing the fire. The fireplace analogy also applies inasmuch that it is necessary to provide an even inflow of oxygen to support the combustion process or heat generating respiration of the composting bacteria. This provides air more effectively to material in the pile than purely random lateral diffusion of gasses from slots in a base beneath the composting material. The air flow is self-sustaining as the aerobic microorganisms generate heat to maintain the convention current, and the convection current provides air to the aerobic microorganisms with which the microorganisms can respire and grow. Under such conditions, the microbial population rapidly and uniformly changes to mostly thermophilic bacteria, capable of producing sufficient heat to inactivate normal gut bacteria (e.g., the gut microbiome), and many other harmful biological forms. The use of specialized geotextile drainage fabric for the aeration distribution, coupled with straw bales for walls and/or gabion cell construction mean that thermopile cells can be constructed on a simple graded surface with minimal capital expense, and essentially considered a consumable part of the process. In addition, the components are of very small volume and easily shipped and stored for military and disaster relief applications.

The heat generated and maintained in the container also can be sufficient, and for sufficient duration, to kill pathogenic microorganisms (pathogens can tend to be from anaerobic gut bacteria, though there are also aerobic forms) so that the resulting compost can be used as fertilizer.

Disclosed herein is a device comprising: (a) a container configured to contain a composition and comprising: (i) insulated walls, (ii) an air intake and (iii) a vent; and (b) a composition contained in the container, wherein the composition comprises aerobic microorganisms, a carbon source and a nutrient source sufficient to support growth of the aerobic microorganisms under aerobic conditions; wherein the container comprises insulation sufficient to retain heat generated by aerobic respiration by the aerobic microorganisms in the composition, and has dimensions configured, to create a stack effect that moves air into the air intake, through the composition and out the vent, and wherein the moving air provides an aerobic environment to the aerobic microorganisms to support growth of the aerobic microorganisms. In one embodiment the carbon source comprises biomass. In another embodiment the biomass comprises straw and paper. In another embodiment the nutrient source comprises excrement. In another embodiment the air intake comprises a top support comprising an air-permeable material on which the composition rests and a bottom support spaced apart from the top support and defining a space between the top and bottom support, said space substantially coextensive with the top support, and at least one air conduit configured to provide air to the space. In another embodiment the vent comprises an opening at a top of the container. In another embodiment, the air flows from the air intake through the composting material to the upper surface in a generally vertical path. In another embodiment the vent is covered with an air-permeable material. In another embodiment the air intake is connected to an external fan. In another embodiment the air intake is connected to an external heat source. In another embodiment the air intake is connected to a source of humid or water saturated air. In another embodiment the air intake is regulated by a valve. In another embodiment the container is configured to contain at least 2 cubic meters, at least 8 cubic meters or at least 20 cubic meters. In another embodiment the insulated walls comprise straw. In another embodiment the walls comprise a baled, fibrous material. In another embodiment the carbon source comprises a material used as insulation in another composting device. In another embodiment the device is configured to promote growth of thermophilic organisms. In another embodiment the device comprises a second container comprising: (i) insulated walls, (ii) an air intake and (iii) a vent, and a composition contained in the container, and comprising a duct communicating between the vent of the first container and the air intake of the second container.

Also disclosed herein is a method comprising: (a) providing a container configured to contain a composition and comprising (i) insulated walls, (ii) an air intake and (iii) a vent; (b) providing, in the container, a composition comprising: (i) aerobic microorganisms, (ii) a carbon source and (iii) a nutrient source sufficient to support growth of the aerobic microorganisms in an aerobic environment; and (c) growing the aerobic microorganisms in the composition by maintaining an aerobic environment, wherein the aerobic environment is provided by maintaining a stack effect that moves air into to the air intake, through the composition and out the vent, wherein the movement of air is maintained by heating air in the container with heat generated by aerobic respiration of the aerobic microorganisms, and contained in the container by the insulation. In one embodiment the method comprises growing the aerobic microorganisms in the composition to produce a climax population of predominantly thermophilic bacteria. In another embodiment the thermophilic bacteria produce heat sufficient to inactivate microorganisms of the human microbiome. In another embodiment the heat generated through aerobic respiration heats the composition to a maximum between 45° C. and 125° C. In another embodiment the aerobic microorganism shifts through a stage promoting mezophilic bacteria and methane producing bacteria and wherein the composting material attains a temperature exceeding the survival temperature range of the mezophilic, methane producing bacteria. In another embodiment aerobic respiration generates heat, and wherein the heat produces a self-sustaining stack effect for at least 7 days or at least 30 days. In another embodiment aerobic respiration generates heat in the container at a sufficient temperature and for a sufficient time to kill pathogenic microorganisms in the composition. In another embodiment growing the aerobic microorganisms for a time sufficient to kill substantially all pathogenic microorganisms in the composition. In another embodiment the nutrient source comprises excrement. In another embodiment the method further comprises detecting one or more operational taxon units in the composition before, during or after growing. In another embodiment, microorganisms in the composition produce methane and the method further comprises ducting air containing methane from the container to a second container configured for composting and wherein a material in the second container removes methane from the ducted air.

Also disclosed herein is a method comprising: (a) collecting human excrement; (b) mixing the human excrement with a carbon source; and (c) composting the mixture in a composting system of this disclosure to create a compost. In one embodiment the human excrement is collected from a public waste facility. In another embodiment the human excrement is collected from a plurality of source locations. In another embodiment the compost comprises no detectable living organisms pathogenic to humans. In another embodiment the method further comprises using the compost as fertilizer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

I. Collection Tank

Figure 1:
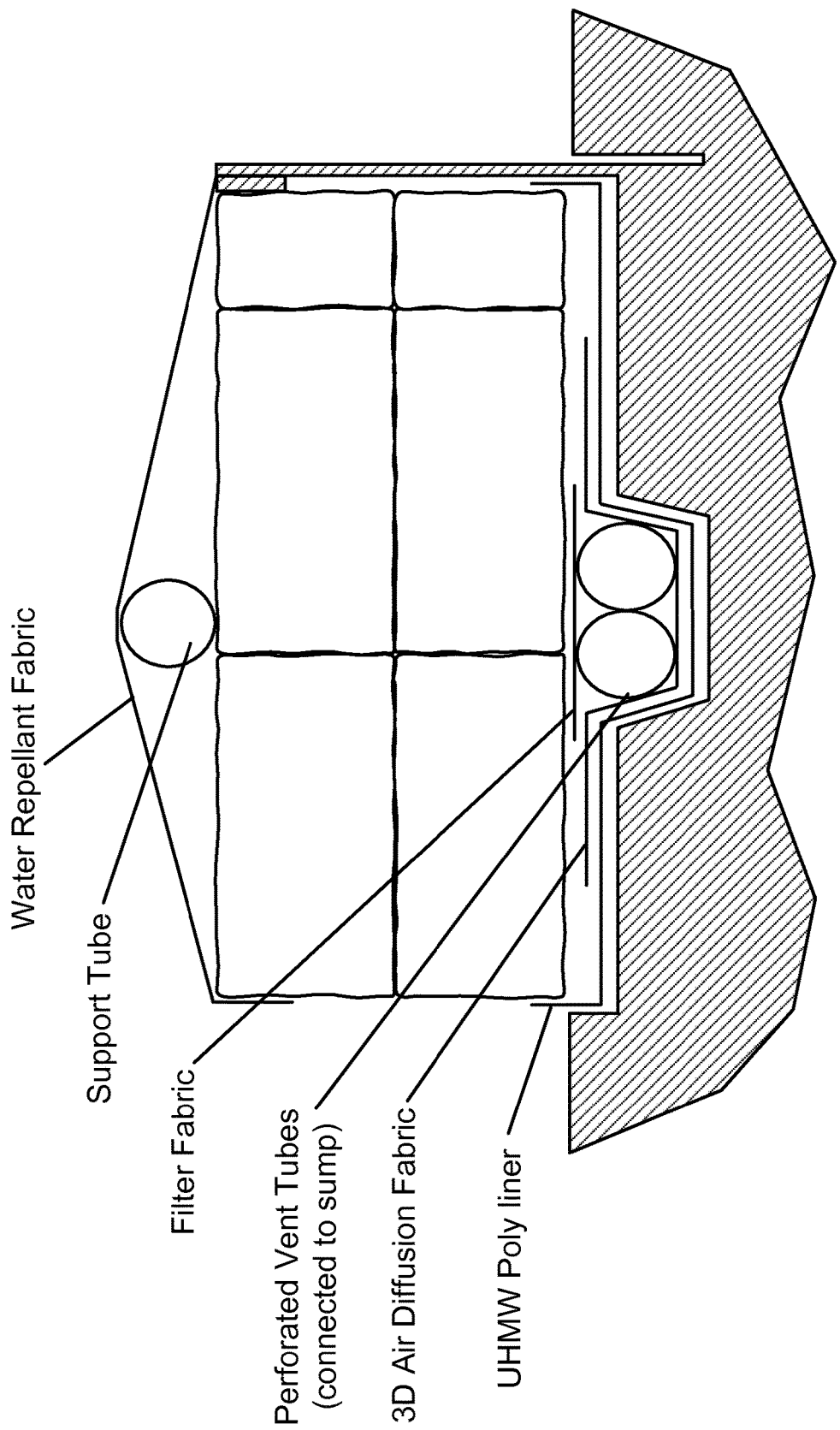
FIG. 1 shows a device of this disclosure. The device includes a container resting on a liner. The floor of the container comprises an air-permeable distribution fabric. Below the fabric are vent tubes in communication with an air source and a sump. The top of the container is covered by a water resistant fabric, but is otherwise open to the passage of air from the vent tubes, through the air-permeable fabric, up the space of the container and out the top, which functions as a vent. Gas can be collected for filtering and scrubbing.

Sanitary waste is collected in a storage tank to await collection pick-up by a vacuum tank truck. The tank incorporates a lid, configured such that when open, allows coupling of the vacuum hose to the tank truck in such a way that the waste is drawn from a tube that projects from the coupling to the bottom of the tank, avoiding insertion of the vacuum collection hose from a collection vehicle into the tank and exposure of the sanitary waste outside the system. When the lid of the tank is open for pumping, an annular ring or other venting means is open to prevent drawing a vacuum on the walls of the tank and the connection to the house, with resultant damage to the system. The tank and collection system are configured to prevent venting of methane and other gasses to the atmosphere. The lid to the collection tank can incorporate multiple filtering media for volatile organic carbons, or alternately, the small volume of gasses can be vented to a soil bed, where microbial activity will digest the methane and other such gasses.

Similar technology can apply to installations in commercial buildings, where there is similar requirement for tank storage. Vacuum collection systems can also be used for housing development type applications. It is possible to insure a slight bleed into the central vacuum system to eliminate discharge of gasses from the household collection system by inducing a very slight negative pressure.

The low molecular weight (16.04 grams per mole) and −161° C. boiling point of methane reduces the effectiveness of carbon absorption, however activated carbon which has been halogenated or sulfonated or certain zeolites can have a high storage capacity for methane.

II. Collection Vehicle

Capital cost of waste treatment equipment is a major barrier to providing a high degree of treatment to sanitary waste, especially in rural areas. For the present disclosure, a multi-use collection vehicle dramatically reduces capital and handling costs. Based on a commercial transfer truck, the basic body is used for collection of greenwaste and other carbon sources, with the transfer function being used to accommodate a vacuum collection tank system. In addition, the composting chambers used in the process can be configured to be compatible with the transfer function. The transfer bodies can be moved using a rail system compatible with the rails on the transfer trailer, which can incorporate scales to facilitate mixing etc.

The transfer trailer compatible composting chambers may be advantageously used where location and environmental conditions make preferable a secure, enclosed batch system, though capital costs may be somewhat higher.

III. Mixing System

Accurate mixing with minimal handling can be achieved by using a modified agricultural vertical feed mixer. Handling of the ultra low flush ("ULF") toilet waste and vault toilet waste, which is very liquid, are considerably different from handling sludge/biosolids filter cake from municipal sewage waste plants, which constitute the majority of large municipal composting facilities.

Cattle feed mixers have scales built in, and include a vertical auger mixer capable of shredding bales and straw in the feed mix. In the present disclosure, the greenwaste/additional carbon source would be added to a known weight, then the liquid waste added to achieve the desired moisture content for the process. Virtually all objectionable odors from the vault toilet waste in the test facility are essentially eliminated by the mixing process. The mixed compost material is then discharged by a modified conveyor system directly into the composting cells.

IV. Composting System

This disclosure provides a composting system configured to produce a self-sustaining and substantially vertical flow of air through a pile of composting material by creating a stack effect. A stack effect (also called the "chimney effect") is a form of convection current that moves gas due to buoyancy due to a difference in inside-to-outside air density resulting from temperature and moisture differences. Such a system relying on stack effect does not require forced aeration, either positive or negative. The system can sustain a vertical current for at least several days, at least several weeks or at least several months, provided that the composting pile contains material sufficient to maintain aerobic respiration. The system is configured such that heat generated by aerobic respiration by microorganisms draws air into the compost pile. Air being drawn through the pile, in turn, provides oxygen to the aerobic microorganisms whose metabolism generates the heat that sustains the convection current.

The composting system is configured so as to provide composting cells with sufficient insulation and height such that, by providing a diffuse air source at the bottom of the container (sometimes referred to as a "composting cell"), the heat generated by the microbial activity induces a vertical flow of air through "stack" effect, thus providing oxygen to fuel the aerobic thermophilic process. The main object of the configuration is to provide an environment where high temperature thermophilic bacteria will predominate as the elevated temperature eliminates the taxa associated with gut bacteria and potential human pathogens. All compost piles will heat up, including anaerobic digestion. Sanitary waste tends to be highly anaerobic, as opposed to much greenwaste and garden composting.

A composting system configured to maintain a self-sustaining upward vertical flow of air through composting pile includes the following elements: First, the composting material in the container is substantially air permeable, that is, not so compressed that it inhibits passage of air. Second, the system is configured to provide air substantially evenly across a bottom surface of the pile, e.g., at substantially even pressure. Third, the container has a top that allows the escape of gas, for example, a top that is open or that is covered with an air-permeable material. Fourth, the container walls are configured to provide sufficient insulation to maintain a temperature differential between ambient temperature and temperature within the pile (FIG. 1). Fifth, the container has height-to-width ratio sufficient to support a generally vertical flow of air from the stack effect within the composting container, for example, having a ratio of height-to-width at the narrowest aspect of at least about 1:2. The system can function in a manner similar to a flue, directing lower density/pressure warmer air inside the container upward toward cooler ambient air above, while drawing higher pressure fresh ambient air in through the bottom, e.g., exhibiting the stack effect.

Figure 2:
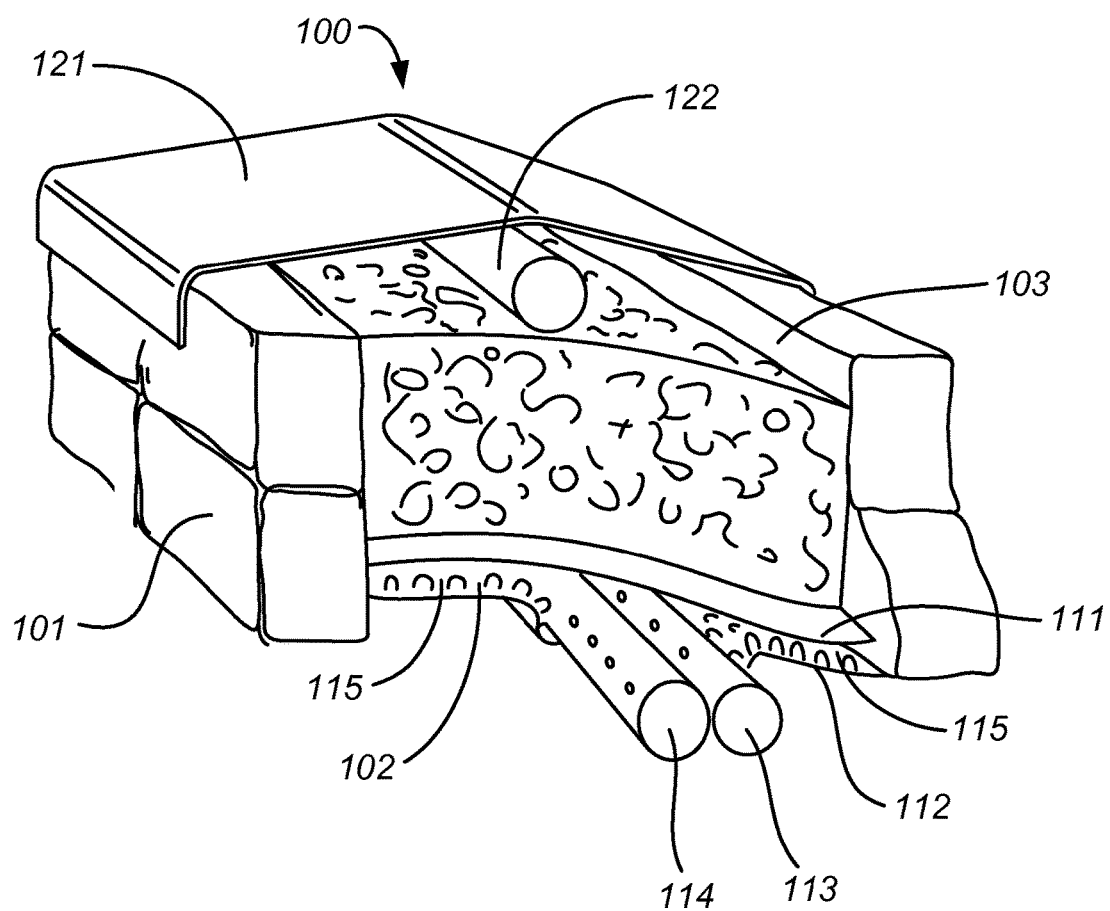
FIG. 2 shows a three-dimensional view of a composting system of this invention.

Referring to FIG. 2, composting system 100 has the following dimensions: Width-2 m, length-2 m, height-1 m. The system includes a composting cell comprising walls 101 made of an insulating material, such as hay bales, stacked on one another. Air intake 102 comprises top support 111, bottom support 112 and air conduits 113 and 114. Top support 111 comprises a layer of air permeable material and functions as a floor on which compostable material rests. Bottom support 112 comprises a layer of dimpled material which top support 111 rests. The dimples allow space 115 between the top and bottom supports. This space extends substantially across the entire bottom surface of top support 111. Air conduits 113 and 114 comprise perforated pipes. They are disposed between the top and bottom supports. Air moved through the conduits can access the entire space. Composting system 100 also includes vent 103 at the top of the container. The top is covered by air permeable cover layer 121, which is supported by structural element 122 (in this case, a pipe).

A. Composting Material

Material to be composted includes a carbon source, a nutrient source (in particular a nitrogen source), water, oxygen and aerobic microorganisms.

(1) Carbon Source

The following items are among those can be used as carbon sources: Greenwaste is biodegradable waste that can be composed of garden or park waste, such as grass or flower cuttings and hedge trimmings, as well as domestic and commercial food waste. Green waste tends to be higher in nitrogen, as opposed to brown waste, which is primarily carbonaceous.

Biomass includes any cellulose- and/or starch-containing raw materials, and is generally useful as a carbon source for composting. Wood chips can be in the form of chips from a chipper (2" fairly consistent) or tub grindings (variety of sizes, some long pieces). They promote natural air flow in the pile. Hay and straw are dried grasses that are a good carbon source. Paper Products, such as cardboard and newspaper, provide carbon and good absorption, but not much airspace. Corn Cob/Stalk can be used to provide a carbon source and provide for more air flow. Leaves and Yard Trimmings (small sticks, waste produce and garden residuals) can be used as a bulking material and carbon source. Wood shavings tend to clump when wet, providing a carbon source but not promoting good air flow. Saw dust has a very fine particle size, providing a good carbon source, but it is very poor in providing air circulation.

(2) Nutrient Source

Aerobic microorganisms require non-carbon nutrients for growth. Primary among these nutrients is nitrogen. However, other elements, such as phosphorus and sulfur also promote growth. These nutrients exist in most materials useful as a carbon source. However, materials rich in these nutrients, particularly nitrogen, can be usefully added to the composting mixture.

In particular, manure and animal excrement are excellent nitrogen sources. Animal excrement includes urine and/or feces. This includes excrement from nonhuman animals as well as human excrement. Human excrement is also known as humanure or night soil. Excrement, and in particular human excrement, can include pathogenic bacteria. These pathogenic bacteria are substantially eliminated by the high temperatures generated by the composting system of this disclosure.

(3) Water

The compostable material may contain natural moisture or water can be added to the material. If liquid excrement is included in the mixture, this material can provide water. Water can be added by means of humidifying the air flowing through the composting material (4) Oxygen Oxygen is supplied as fresh air from the air intake described herein. Fresh air replaces stale air (that is, air from which oxygen has been depleted by aerobic respiration) through the stack effect within the composted material.

(5) Aerobic Bacteria

Aerobic bacteria are naturally occurring in the environment. They typically will exist within any material useful as a carbon source, such as greenwaste, and also in sanitary waste in sufficient quantities to inoculate the mixed composting mass. However, there may be specific organisms that may assist in the breakdown of given compostable material or enzymatic materials might accelerate the breakdown of certain materials.

B. Dimensions

A composting system of this disclosure has a volume and dimensions consistent with maintaining a thermal convection current through the composting pile. One factor limiting volume is over-compression of the compostable material due to weight. That is, under sufficient pressure, the compostable material can become sufficiently compressed that it becomes too dense to support the flow of air through it and becomes deprived of oxygen. It is believed that when typical compost materials are used, such as greenwaste, over-compression will not occur at heights of up to at least 4 meters. In situations in which over-compression selection can occur, the composting cell can be partitioned with supporting material, such as wire mesh, and stages, supporting portions of the compostable material throughout the height of the system.

Thermal convection through the pile can be maintained when the pile has a height:width ratio of at least any of 1:2, 1:1, 2:1, 3:1, 4:1. In this case, "width" refers to width of the pile at its narrowest aspect. It is believed that as long as the height:width ratio is maintained, the pile can assume any length. So, for example, a pile of height 1 m can have a width of no more than about 2 m, and preferably less than this. Such a pile could have a width at its base of about 2 m and a length of at least any of 2 m, 3 m, 4 m or more. A pile of height 2 m can have a width at its base of no more than about 4 m. Such a pile could have a width at its base of about 4 m and a length of at least any of 4 m, 6 m, 8 m or more. In one embodiment, the compartment can have internal dimensions of about 8'L×6'6"W×4'H.

In certain embodiments, the container can be extended linearly as long as practical, as long as the width and height have the proper aspect ratio, which would prevent short-circuiting of airflow through the pile.

Accordingly, certain embodiments the composting system is configured to contain a volume of composting material of at least any of 2 $m^3$, 5 $m^3$, 15 $m^3$, 20 $m^3$, 25 $m^3$ or 40 $m^3$.

C. Wall

The composting system includes a wall configured to contain the composting material and to provide insulation. The walls are oriented vertically so as to create a vertically oriented chamber, open at the top. The insulation is sufficient to maintain a temperature differential between ambient and the composting material inside the container to create a stack effect inducing vertical currents through the composting material. Typically, this temperature differential needs to be at least 4° C. In temperate climates, where the system has a height:width ratio of no more than 1:2, the insulation can be at least any of 15 $(m^2K)/W$, 20 $(m^2K)/W$, 35 $(m^2K)/W$, 50 $(m^2K)/W$, 60 $(m^2K)/W$. Insulating materials typically used in construction can be used. These include, without limitation, natural fibers (e.g., straw (hay bales), shredded paper, bagasse, hemp, cotton and wool), fiberglass, cellulose, plastic fiber, polystyrene and closed cell polymer foams. The degree of insulation necessary can depend on the size of the pile and the climate. Insulation can provide a dual purpose. First, when it is sufficient to maintain at least a 4° C. temperature differential between the pile and ambient temperature, this will generate a self-sustaining air current in the composting material. Second, when it is sufficient to maintain temperatures above about 45° C., this will kill pathogenic microorganisms in the composting material. Thus, the absolute amount of insulation can be sufficient to retain enough heat in the composting cell to generate a thermal gradient that creates the stack effect, and in certain embodiments, raising the temperature throughout the pile sufficiently to eliminate pathogenic bacteria. The insulation also can be sufficient to maintain temperatures in the composting cell of at least any of 45° C., 50° C., 60° C., 70° C., 80° C., 90° C., 100° C., 110° C. or 120° C., e.g., sufficient to kill pathogenic microorganisms in the composting material.

In one embodiment, walls can be made of a cellulosic material. The material can be formed into building blocks, such as bales. For example, the walls can comprise bales of hay or shredded paper stacked on one another. One property of such material is that after use, a structural material then can be used as a carbon source in another composting system.

The use of straw or other bales of compostable material to form the composting cells and to induce aeration can later themselves be incorporated into the process advantageously as the carbon source for subsequent batches. In addition, rather than bales, the compostable material may be contained in collapsible wire structures like construction gabions.

Thus, shredded paper waste and other materials can be used to provide the insulating properties necessary for the process. Likewise, the cages could incorporate fabrics and insulated faces to further control performance.

D. Air Intake Assembly

A composting system includes an air intake assembly configured to supply an oxygen-containing gas, such as air, to the composting pile in such a way that air moves primarily vertically, rather than diffusing horizontally and unevenly through the pile, which creates zones where there is insufficient oxygen for the composting process. In certain embodiments, the air intake supplies air across substantially the entire bottom surface of the pile of compostable material. If air is supplied to too small an area at the bottom of the pile, once entering the pile, it will tend to diffuse laterally, rather than creating an up-draft. Accordingly, increasing the amount of the bottom surface area of the pile having access to air promotes creation of a convection air upward. Heat generates a stack effect which, in turn, supplies oxygen to aerobic microorganisms to continue generating heat. Such an air intake can include a top support comprising a material permeable to air on which the compostable material rests, a bottom support spaced apart and under the top support and, together with the top support, defining a space substantially coextensive with the top support, and one or more conduits configured to move air into the space. Together, these elements are configured to move air from an outside source into the space, to distribute the air across the under surface of the top support and to allow the air to move through the top support and into the compost pile. The air intake assembly can function as plenum, moving air into the space through positive outside pressure (e.g., a pump) or through negative pressure supplied by the convection current produced by the thermal stack effect of the heat generated by the composting material. The top support can function as an air permeable floor of the composting cell, supporting the compostable material.

Air moves primarily vertically when the space under the floor extends substantially to the perimeter of the walls of the composting cell. Thus, supplying air to the top support near the perimeter of the composting cell supports vertical flow of air through composting material near the perimeter of the composting cell. So, for example, the space can extend to at least any of 70%, 80%, 90%, 95%, 98%, 99% or 100% of the wall-to-wall diameter of the floor.

(1) Top Support

The top support of the air intake assembly includes a top side and bottom side. Compostable material deposited into the composter rests on the top side of the top support. The bottom of the top support has a surface communicating with a space and over which air can be substantially evenly distributed. Said space also serves as an air gap to prevent loss of heat from the composting material to the ground by conduction.

The top support can comprise any solid material permeable to air. Many materials useful as flooring materials can be used and are known in the art. These include, for example, three dimensional plastic supports combined with geotextiles. Plastic grids with a permeable top layer suitable as a top support include, for example, ECOFLEX® (Alberta, Calgary, CA) and ECOGRID (Terrafirm Enterprises). Some of these are also referred to as stabilizing grids. Suitable geotextiles, and in particular woven and/or perforated geotextiles, include, for example, GEOTEX® (PROPEX™, Chattanooga, TN), TERRATEX (Hanes, Winston-Salem, NC) and similar items available from DuPont and US Fabrics (Cincinnati, OH).

(2) Bottom Support

The bottom support can be a layer of material, e.g., an elastomer, placed under the top support. Such a layer is configured to define a space or plenum between the layer and the top support (which forms the roof of the chamber).

In one embodiment the bottom support can have a texture or three-dimensional surface. In one embodiment the bottom support can comprise a sheet with multiple support posts, that is, a dimpled layer of material, e.g., a sheet drain. When overlaid with the top support, the dimples create the space between the two supports. The dimpled lower support can be formed from a sheet of thermoplastic such as ABS, comprising a continuous impervious sheet.

In another embodiment, the lower layer comprising the bottom support can comprise EPDM (ethylene propylene diene monomer (M-class)) rubber laid on level ground. There can be an intermediate layer comprised of a grid comprised of longitudinal and lateral ribs, with interconnecting holes in the ribs to permit unrestricted airflow between the small cells formed by the ribs, which in turn support an upper layer of permeable fabric.

It is advantageous to have the bottom support sheet continue several inches up the inside wall of the chamber, thus forming a water tight basin for the collection of leachate.

In another embodiment, the spacing between the upper layer of permeable cloth is spaced from the lower layer by multiple perforated tubes of small diameter (1-2" laid parallel to each other over the entire lower surface and covered by an upper layer of air permeable fabric.

In a further embodiment, the lower floor of the chamber comprises a series of three dimensional tiles comprising a multiplicity of small cells connected laterally between the walls of the cells, with the tiles interlocking together, such they can be removed for cleaning when necessary. The edge of the tiles may be configured to interlock with adjacent tiles and/or the air conduit providing the air supply. The upper surface of each composting cell may be closed with downward facing plastic fingers which prevent the composting material from blocking the airflow beneath the upper surface while providing additional surface for air flow, and reducing risk of compaction. The upper surface of the tile may also be closed with a permeable fabric, retained in place by clips or other devices such that it may be replaced if worn or damaged. In such designs the transverse edge of the tiles comprising the bottom of the composting cells may be raised to perform a guide for shovels and equipment buckets to protect the face of the top surface from damage when loading and unloading the composting material.

Alternatively, the bottom support can be a platform, e.g., a flat platform, such as a slab or the ground. In such a case, the bottom support is further provided with space-creating supports. For example, the container can rest on stilts so that a space is created between the bottom and top supports.

(3) Air Conduit

The air conduit is configured to supply air from an outside source to the space beneath the top support. In certain embodiments the air conduits comprise perforated pipes communicating with air outside the space and channel air into the space. Perforated pipes are available commercially as drainage pipes. In systems of this invention having volumes between about 2 m$^3$ and 20 m$^3$, perforated pipes can have a diameter of about 6 inches and can have perforated holes having diameters of about ¼ inch.

If the periphery of the top support is raised apart from the bottom support, the air intake can comprise the openings between the two supports.

The air conduit can also be used to supply a heated source of air from an external heat source or mixed with air ducted from the vent of a second compost pile that has already reached thermophilic temperatures. This can be advantageous to produce the stack effect when the initial temperature is sufficiently low to inhibit the start of the microbial activity.

The air conduit can also be connected to a humidifier to maintain a level of moisture within the composting material to avoid excessive dryness, which would inhibit the composting process. The central aeration pipes also provide a collection system for any leachate, which may be recycled back into the composting cell.

(4) Air Pump

A composting system can include an air pump configured to deliver air at positive pressure into the space between the air conduits and the top support. Such an air pump can assist in initiating fresh air flow to the compost pile. However, it is not necessary for thermal convection to be self-sustaining. The air pump can be driven with solar energy.

A very low pressure (@½" water column) provided by a fractional horsepower solar fan can be used to facilitate start of the stack effect flow process.

E. Vent

A composting system also includes a vent through which air can leave the compost pile, e.g., through an opening at the top. The vent also can comprise a layer of air permeable material that covers the compost pile. The vent can also comprise a gas impermeable cover and collection pipe such that the heated air being vented can be ducted to the air pump and mixed with air feeding a second compost structure, or ducting the air containing methane from the mezophilic stage of a first composter to a second composter which has entered the thermophilic stage and serve as a biofilter for the removal of the methane.

V. Composting Method

A. Process

This disclosure provides a method of producing compost. The systems of this disclosure generate compost more quickly than other systems. Also, compost made by these methods from starting materials that include animal excrement is substantially free of microorganisms pathogenic to humans. Such pathogens do not survive the high temperatures generated by this system.

Composting materials, including carbon source, a source of nutrients and water are combined in a container of the system of this disclosure. The container may be covered with an air permeable material. Optionally, an air pump can blow air into the space below the container top support. This can help initiate supply of air to the compost pile for the thermal gradient to be established and the stack effect to become active in generating air flow. Aerobic microorganisms in the pile metabolize the carbon source and the nutrients, generating water, carbon dioxide and heat. Heated air in the pile is less dense than cooler air, and, therefore, rises, drawing fresh air from the space, through the pile, and out through the vent. Because fresh air is delivered evenly to the entire surface of the top support that supports the composting material, microorganisms throughout the horizontal cross-section of the container have access to oxygen. Insulation in the walls of the container inhibits the loss of heat. With proper amounts of insulation, temperatures near the wall of the composting cell will not differ very much from temperatures at the core of the container. Also, a temperature differential between the inside of the container and the outside of the container is maintained.

As metabolism increases, and heat is retained in the composting cell, e.g., by the insulation, a thermal gradient is established, with temperature decreasing from the bottom of the pile to the top. The heat gradient establishes a stack effect pulling fresh air into the pile from the air intake and expelling the heated air. Air from which the bacteria have consumed the oxygen vents at the top of the pile. A temperature differential of 4° C. suffices to establish convection current. As long as the aerobic microorganisms have oxygen and substrates for growth, they will generate heat. As long as the aerobic microorganisms are generating heat, the vertical flow current is maintained, making the convection current self-sustaining.

The insulated composting chamber that can achieve temperatures in excess of 70° C. for extended periods of time with no energy input, relying only on the heat produced by microbial activity for sanitation. These temperatures greatly exceed U.S. State and Federal Standards for composting of biosolids (sludge from municipal waste treatment plants) while completely eliminating human and animal pathogens due to high temperatures. The compost chambers are designed so that an air source is diffused across the bottom of the pile and produces an upward air flow throughout the pile, providing oxygen for the decomposition of the waste and achievement of the necessary temperatures. In the process, the incoming sanitary waste, is mixed with locally available greenwaste or sorted solid waste to produce a mix of specified moisture content, and then placed in the thermophilic compost chambers. While the chambers themselves can be permanent fixtures, significant capital structure is not required, as it is advantageous to construct them from baled and sorted municipal waste or straw that provides the insulation necessary for the process. The bales themselves can be recycled into the process as a carbon source after several cycles of use. The chambers can be built on an impermeable groundwater barrier, over which the aeration pipes and diffusion fabric are placed. The material is then placed into the chamber, and the whole assembly covered with a composting fabric that allows rainwater to run off and air to pass. The separated sanitary waste can come from commercially available ultra-low flush (ULF) toilets, such as those used in the marine industry and increasingly in Scandinavia, which use less than 6 fl. oz of water per flush and can incorporate a vacuum pump/comminutor system to deliver the sanitary waste to a collection tank before addition to the compost chambers. This represents a water savings of 98.7% over the average EPA 3.5 gallon flush. The toilets are a direct replacement for conventional toilets, requiring minimal modification to plumbing, other than a pumped connection to the storage tank. Odor control is provided by vent filters on the storage tank. The thermopile system has been tested with vault toilet waste from the U.S. National Park Service, typical of waste from the 90,000 U.S. Army Corps of Engineers public camp sites.

Figure 3:
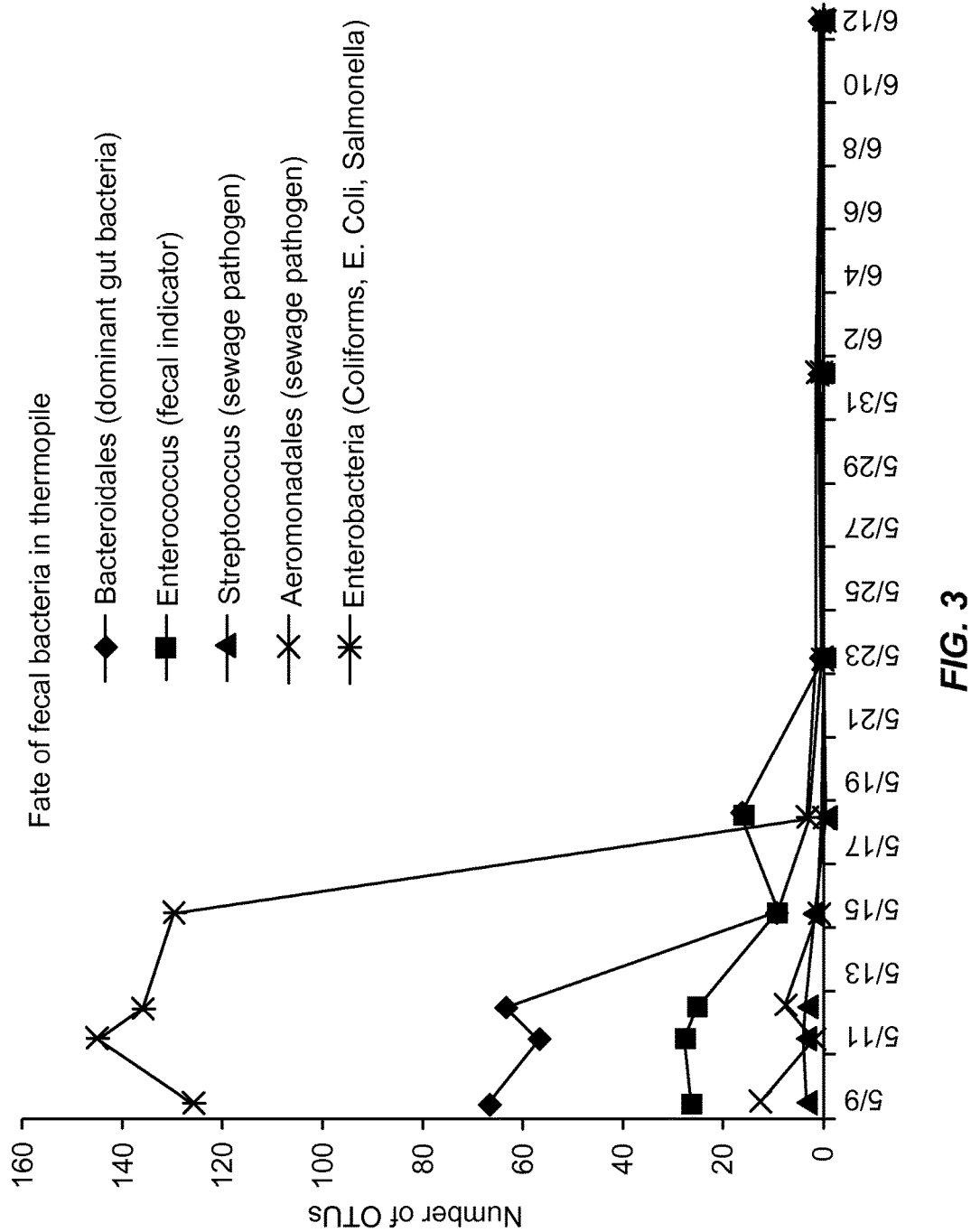
FIG. 3 shows a chart of the fate of various phyla of bacteria containing pathogens in a pile of a system of this disclosure over time.

Temperatures in the container increase rapidly from ambient to between 45° C. to 70° C., often in as little as 29 hours. Over the course of days and weeks at these temperatures, thermophilic aerobic microorganisms are selected for, while anaerobic and gut pathogenic microorganisms are selected against. At the conclusion of the process the compost is substantially free of microorganisms pathogenic to humans. See, e.g., FIG. 3, which shows amounts of various potentially pathogenic bacteria over time.

As the bacterial population shifts to the thermophilic aerobic forms, it passes through the mezophilic heat range (20°-45° C.) which is favorable to methane producing bacteria. Therefore it is an object of the invention to provide an environment wherein the heat of the microbial activity is elevated beyond the mezophilic heat range as quickly as possible, thus minimizing production of methane, a greenhouse gas.

It is possible to pre-heat the air in colder climates to speed up the microbial activity until it is self-sustaining at sufficient levels of microbial activity. Increased insulation also helps, and it can be possible to stage composting cells so that the exhaust air from a pile at high temperatures is exhausted and mixed with the intake air source of a compost pile that is just starting, either directly or through an air-air heat exchanger, allowing full atmospheric oxygen levels in the plenum of the starting pile.

It is possible to reduce methane production by ducting air from a first pile that is going through mezophilic temperatures with a tendency of the population to produce methane, and duct it to a pile that has already reached thermophilic temperatures and would consume methane.

During and after composting, waste material can be tested for the presence of various microbial forms. For example, the PhyloChip microarray performs a single test that is capable of simultaneously identifying any of 60,000 taxa, or species of bacteria. (See, e.g., U.S. Patent Application 20120165215 (Anderson et al.).)

EXAMPLES

Waste Collection

Sanitary waste can be collected from 20 housing units equipped with ULF toilets every 2 weeks. Minimal handling is then required for compost pile construction. The sanitary waste is mixed with a defined amount of greenwaste (food waste, wood chips, sawdust, straw) using a modified, agricultural vertical feed mixer. This improves moisture content and aerobic structure. The mixer includes scales to measure the correct ratios of components and its output conveyor allows placement of the mixed material directly into the composting cell, thus eliminating handling and minimizing operator exposure to the waste. The pile is then continuously monitored for temperature, oxygen and moisture, and periodically sampled for microbial community and pathogen analysis. Thermophilic temperatures are typically achieved within the first 3-4 days and persist for at least one month before removal of finished compost material that is certified pathogen-free. This complies with existing U.S. regulations before application to agricultural lands, and for landscaping and soil admixture preparation.

The system can also include a tank to collect a given quantity of waste, which is then mixed in a container (optionally one of a series) pre-loaded with sufficient carbon source material such that the desired bulk density of the material is achieved when mixed with the given quantity in the tank.

One mixing device can service each container as the sanitary waste is added, and then be moved to the next container until a sufficient charge of sanitary waste is achieved.

After the mixed containers have finished their composting cycle, they can be removed and the composted material used as seen fit. Unlike other on-site composting systems, this eliminates the problems of leachate and assures the correct mix for composting.

This type of system can be of particular advantage in large facility/high rise developments, especially in third world and emerging nations, where the conventional sanitary structure to protect the environment is not available, or costs are excessive.

Composting System Assembly

Preparation of level area of ground for construction of composting cells.

1. Trench for aeration pipes and grade floor of composting cell with a slight slope towards trench.
2. Lay three dimensional fabric comprising plastic base and bonded cloth cover, plastic side down to cover the majority of the bottom of the composting cell to create an air plenum covering the lower surface of the composting cell. A commercial drain fabric is used. The fabric achieved very high flow rates. This low resistance allows fabric to act as a plenum, creating even pressure over the lower surface of the composted material. See world wide web site americanwick-.com/products/product_cat_detail.cfm?prod_cat_id=26.

An alternative method is to use plastic grid on EPDM sheet to create a plenum.

3. Lay perforated air supply pipe along trench over cloth surface of the pipes so that air can flow from the pipes into the plenum created underneath the pile by the fabric. Aeration tubes will also collect leachate, if any, that can be pumped out from ends of pipes and distributed on top of compost material.
4. Cover upper surface of pipe with geotextile cloth to prevent compost from plugging vent perforations within the pipes.
5. Attach vent pipes to inlet provided with small (5-10 w) electric fan to provide slight positive pressure in plenum. 1"-2" water pressure or 0.036-0.072 psi at the start of the process, avoids formation of anaerobic conditions in pile admixture before sufficient heat is generated from microbial activity to promote a thermo-siphon flow from the plenum to the cooler ambient air above the pile.
6. Assemble walls of bales or other material around periphery of composting cell.
7. Mix sanitary waste with carbon source in mechanical mixer. Load at waste/carbon source into mixer and add liquid sanitary waste to 60% moisture. The composting material should still be air permeable yet only drain small amount of liquid when squeezed in suitably gloved hand. Place in composting cell.
8. The material can be covered with about 6" of previously composted material as an insulation blanket.

Figure 4:
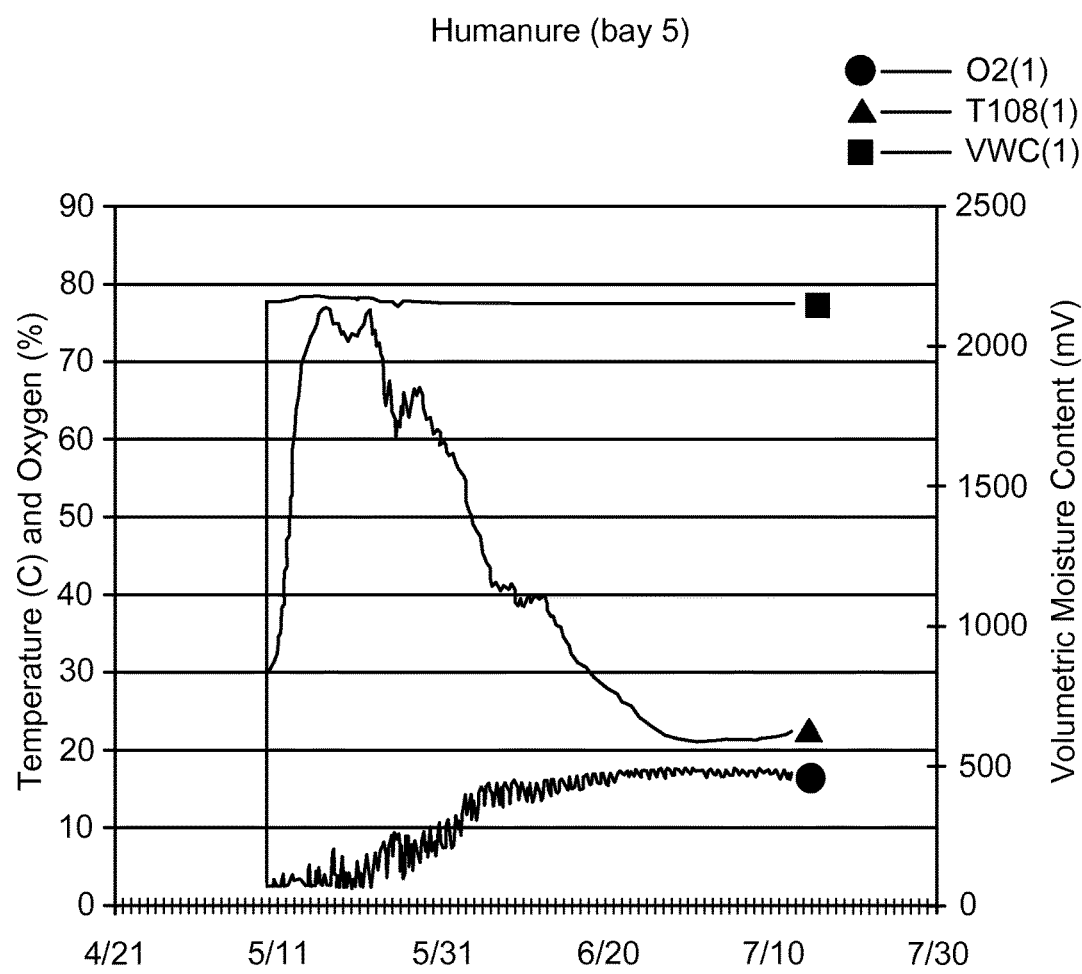
FIG. 4 shows oxygen content, temperature and moisture content in a pile of a system of this disclosure over time. Temperature is seen to rise from about 30° C. to over 70° C. over the course of about a week, and then to fall during the next two months. Microbial activity produces the following results on human waste. Compost continues to break down carbon source material such as paper/woodchips for several months, and would eventually be supplemented by a fungal population. "VMC" refers to volumetric moisture content.

Microbial activity produces the following results on human waste provided by the U.S. National Park Service (FIG. 4). Further composting continues to break down carbon source material such as paper/woodchips for several months, and would eventually be supplemented by a fungal population.

While preferred embodiments of the present invention have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the invention described herein may be employed in practicing the invention.

What is claimed is:

1. A device comprising:
   (a) a container configured to contain a composition, wherein the container has a volume of at least 2 m$^3$ and a height:width ratio of at least 1:2, and wherein the container comprises:
      (i) insulated walls providing insulation of at least 15 (m$^2$K)/W,
      (ii) an air intake, and
      (iii) a vent over the composition provided by the container being open across its top; and
   (b) a composition contained in the container, wherein the composition comprises aerobic microorganisms, a carbon source and a nutrient source sufficient to support growth of the aerobic microorganisms under aerobic conditions, wherein the composition has a temperature of at least 70° C.;
   wherein the air intake comprises a top support comprising an air-permeable material on which the composition rests, and a bottom support spaced apart from the top support and defining a plenum between the top support and bottom support, said plenum supplying air across substantially the entire bottom surface of the composition, and at least one air conduit configured to provide air to the plenum.

2. The device of claim 1 wherein the carbon source comprises biomass.

3. The device of claim 2 wherein the biomass comprises straw or paper.

4. The device of claim 1 wherein nutrient source comprises excrement.

5. The device of claim 1 wherein the vent is covered with an air-permeable material.

6. The device of claim 1 wherein the air intake is connected to an external fan.

7. The device of claim 1 wherein the insulated walls comprise straw.

8. The device of claim 1 wherein the container is configured to contain at least 8 cubic meters.

9. The device of claim 1 wherein the container is configured to contain at least 20 cubic meters.

10. The device of claim 1 wherein the top support comprises a geotextile.

11. The device of claim 1 wherein the bottom comprises a dimpled sheet.

* * * * *